United States Patent [19]

Prabhu et al.

[11] Patent Number: 5,618,866
[45] Date of Patent: Apr. 8, 1997

[54] NEO DIOL PHOSPHITE ESTERS AND POLYMERIC COMPOSITIONS THEREOF

[75] Inventors: Vaikunth S. Prabhu, Vienna, W. Va.; Carloss L. Gray, Belpre, Ohio

[73] Assignee: General Electric Company, Pittsfield, Mass.

[21] Appl. No.: 589,832

[22] Filed: Jan. 22, 1996

[51] Int. Cl.$^6$ .......................... C07F 9/6574; C08K 5/527
[52] U.S. Cl. .......................................................... 524/117
[58] Field of Search ................................ 524/117; 558/85

[56] References Cited

U.S. PATENT DOCUMENTS

| | | |
|---|---|---|
| 3,039,993 | 6/1962 | Friedman . |
| 3,056,823 | 10/1962 | Hechenbleikner et al. . |
| 3,264,247 | 8/1966 | Friedman . |
| 3,281,381 | 10/1966 | Hechenbleikner et al. . |
| 3,305,520 | 2/1967 | Fritz et al. . |
| 3,305,526 | 2/1967 | Guttag . |
| 3,342,767 | 9/1967 | Buckley . |
| 3,415,906 | 12/1968 | Shepard et al. . |
| 3,437,720 | 4/1969 | Guttag . |
| 3,441,633 | 4/1969 | Friedman . |
| 3,467,733 | 9/1969 | Dever et al. . |
| 3,482,002 | 12/1969 | Dever et al. . |
| 3,483,147 | 12/1969 | Friedman . |
| 3,488,407 | 1/1970 | Schall . |
| 3,509,091 | 4/1970 | Cleveland et al. . |
| 3,558,554 | 1/1971 | Kuriyama et al. . |
| 3,646,173 | 2/1972 | Gordon et al. . |
| 3,714,302 | 1/1973 | Dever et al. . |
| 3,794,629 | 2/1974 | Eimers et al. . |
| 3,845,168 | 10/1974 | Guttag . |
| 4,086,304 | 4/1978 | Hutton et al. . |
| 4,196,117 | 4/1980 | Spivack . |
| 4,276,233 | 6/1981 | Markezich et al. . |
| 4,318,845 | 3/1982 | Spivack et al. . |
| 4,405,739 | 9/1983 | Kinson . |
| 4,529,533 | 7/1985 | Chasar . |
| 4,708,979 | 11/1987 | Pedrazzetti et al. . |
| 4,755,546 | 7/1988 | Hechenbleikner et al. . |
| 4,782,170 | 11/1988 | Bae et al. . |
| 4,882,374 | 11/1989 | Wang et al. . |
| 4,956,406 | 9/1990 | Myers et al. . |
| 4,957,954 | 9/1990 | Iizuka et al. . |
| 5,342,869 | 8/1994 | Stoll et al. ............................ 524/117 |
| 5,364,895 | 11/1994 | Stevenson . |
| 5,414,033 | 5/1995 | Nesvadba ................. 524/117 |

FOREIGN PATENT DOCUMENTS

| | | |
|---|---|---|
| 2087399 | 5/1982 | United Kingdom . |

OTHER PUBLICATIONS

Phosphorus and Sulfur,(1983), vol. 15, pp. 9–13.

*Primary Examiner*—Veronica P. Hoke

[57] ABSTRACT

A phosphite and stabilized thermoplastic composition comprising the phosphite where the phosphite has the formula:

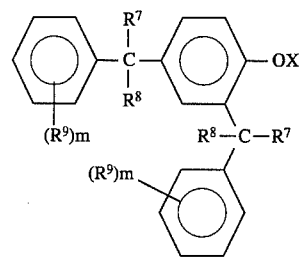

In the above compound, $R^7$ and $R^8$ are preferably alkyl of from 1 to 6 carbon atoms, most preferably an unsubstituted alkyl group. $R^9$ is preferably alkyl of 1 to 12 carbon atoms. m is from 0 to 5. The dicumyl group includes the OX groups which are the phosphite portion. The OX group is hindered by only one alkylaryl group at the ortho position with the other ortho position being occupied by hydrogen. X has the following formula:

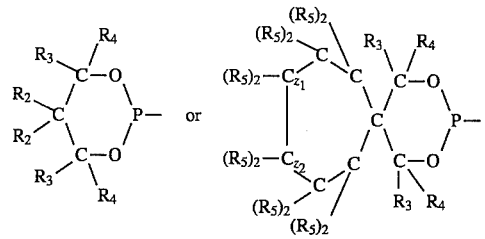

wherein $R_2$ is independently selected from the group consisting of alkyl groups having from 1 to 12 carbon atoms. $z_1$ and $z_2$ can be 0 or 1. $R_3$, $R_4$ and $R_5$ are independently selected from the group consisting of hydrogen, halogen, or alkyl of from 1 to 3 carbon atoms.

14 Claims, No Drawings

NEO DIOL PHOSPHITE ESTERS AND POLYMERIC COMPOSITIONS THEREOF

BACKGROUND OF THE INVENTION

1. Field of the Invention

The present invention relates to phosphites, and more particularly related to aromatic cyclic phosphites which contain a neo substituted carbon group and stabilizing compositions and stabilized resin containing such phosphite compositions.

2. Description of the Related Art

U.S. Pat. No. 3,415,906 describes cyclic phosphites of the formula:

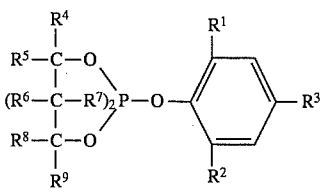

In this patent, $R^1$ and $R^2$ are set forth as being alkyl of 3 to 12 carbon atoms, aralkyl having from 7 to about 15 carbons, $R^3$ is selected from the group consisting of hydrogen, alkyl having from 1 to 12 carbons, aralkyl having from 7 to 15 carbons, halogen, and lower dialkyl tertiary amino. U.S. Pat. No. 3,467,733 to Dever et al describes cyclic phosphites and diphosphites, such as bis(1,3,2-dioxaphosphorinanyl-2-oxy)aryl alkanes, and mono- and bis(1,3,2-dioxaphosphorinanyl-2-oxy)benzenes, useful as stabilizers for organic compositions, such a rubber and polyvinyl chloride. Note that column 3, lines 63 to 65 states: It is preferred to employ hydroxy compounds or phenols which do not have hindered 2,6-substitution on the benzene ring. U.S. Pat. No. 5,364,895 to Stevenson describes bis(aralkylphenyl)pentaerythritol diphosphites of low volitility.

Many of these phosphites can, however, experience thermal stability problems, hydrolytic stability problems, and/or ultraviolet light discoloration problems. Hence, there still remains a need to enhance the various properties of phosphite compositions and find economical phosphite compositions.

SUMMARY OF THE INVENTION

The present invention relates to aromatic dicumyl phosphites of the formula:

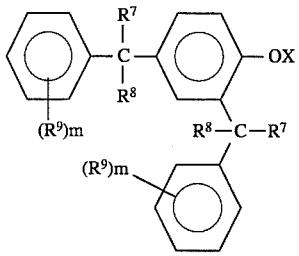

In the above compound, $R^7$ and $R^8$ are preferably alkyl of from 1 to 6 carbon atoms, most preferably a straight chain alkyl group. $R^9$ is preferably halogen, or alkyl of 1 to 12 carbon atoms. m is from 0 to 5.

The dicumyl group includes the OX group which is the phosphite portion. The OX group is hindered by only one alkylaryl group at the ortho position with the other ortho position being occupied by hydrogen. X has the following formula:

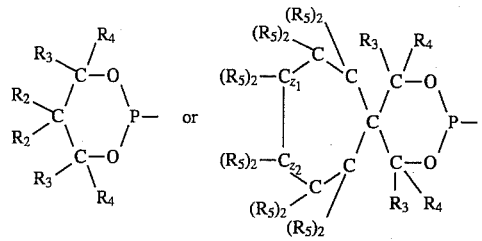

wherein $R_2$ is independently selected from the group consisting of alkyl groups having from 1 to 12 carbon atoms. $z_1$ and $z_2$ can be 0 or 1. If $z_1$ and $z_2$ are both 0, the ring is a five member ring. If one of $z_1$ or $z_2$ are 1 and one is 0, the ring is a six member ring. If $z_1$ and $z_2$ are both 1, the ring is a seven member ring. $R_3$, $R_4$ and $R_5$ are independently selected from the group consisting of hydrogen, halogen, or alkyl of from 1 to 3 carbon atoms. Preferably, the $R_3$ groups are hydrogen. It is preferable for the alpha-carbon in the ring structure to include as least one hydrogen substituent. As explained more fully herein, the above phosphite entities are typically formed from 1,3 alkane diols with the beta or 2 position being blocked by alkyl or cyclic alkyl groups.

The phosphites, which are useful to stabilize organic materials against thermal oxidative degradation, exhibit enhanced hydrolytic stability and are resistant to UV yellowing. The present invention further includes an amorphous phosphite composition containing the above phosphite and stabilizing blends therefrom.

DETAILED DESCRIPTION OF THE INVENTION

In as previously set forth, the present invention relates to phosphites of the formula:

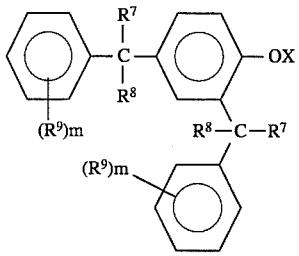

In the above compound, $R^7$ and $R^8$ are preferably alkyl of 1 to 3 carbon atoms, most preferably a straight chain alkyl group. $R^9$ is preferably alkyl of 1 to 12, more preferably 1–4 carbon atoms. m is from 0 to 5, more preferably 0.

The preferred cyclic phosphite moiety, X, of the phosphite compound as set forth above has the following most preferred formulae:

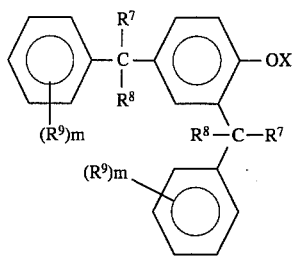

wherein $R_2$ is independently selected from straight chain alkyl groups having from 1 to 6 carbon atoms, or, the phosphite which includes cyclic alkane moieties of the formulae:

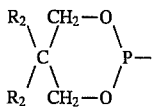

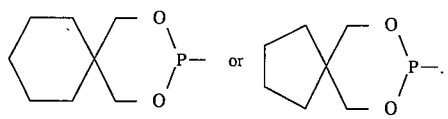

The first step in the production of the phosphite ester of the present invention, is to react an appropriate diol with $PZ_3$ where Z is halogen, preferably Br or Cl. $PCl_3$ is the preferred reactant.

As previously mentioned, the diols utilized are the 1,3-alkane diols wherein the 2 position is blocked. The neo-type glycols are those glycols having beta or the 2,2 positions completely substituted. These diols have the formula:

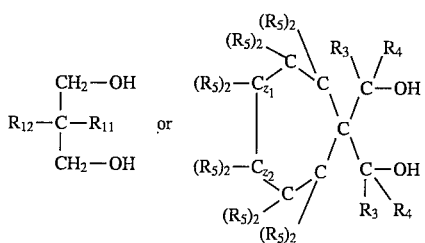

in which $R_{11}$ and $R_{12}$ are alkyl groups of 1 to 12 carbon atoms or and the cyclic formula has the substituent groups as hereinbefore described.

Specific alkyl diols that may be utilized include 2,2-dimethyl-1,3-propane diol, 2,2-diethyl-1,3-propane diol, 2,2-dibutyl-1,3-propane diol, 2-methyl-2-ethyl-1,3-propane diol, 2-ethyl-2-propyl-1,3-propane diol, 2-ethyl-2-butyl-1,3-propane diol, 2-hexyl-1,3-propane diol, 2-methyl-2-hexyl-1,3-propane diol such diols are set forth in lines 7 to 43, column 2, of U.S. Pat. No. 3,714,302 to Dever et al. In addition to those diols, cycloalkyl-1,1-dimethanol where the cycloalkyl group is from 4 to 7 carbon atoms, such as cyclohexane-1,1-dimethanol may be utilized.

The resulting product is an intermediate phosphorohalidite product of the formula:

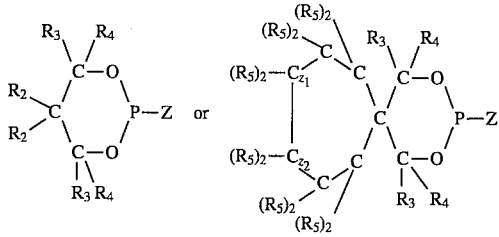

where the R values are as previously described.

The reaction between the diol and $PZ_3$, where Z is halogen, preferably Br or Cl, to form the intermediate phosphorohalidite may be carried out with or without the use of a solvent. Typically $PZ_3$ can be added to the diol or the diol can be added to $PZ_3$. Preferably the $PZ_3$ is added to the diol with the reaction mixture being maintained at a temperature of about 5 to 50 degrees Centigrade. This temperature may be controlled by controlling the rate of $PZ_3$ addition. A slower addition favors lower temperatures. It is preferred to cool the reaction mixture during the addition. A slight excess of stoichiometric amounts of $PZ_3$ is preferably utilized. The reaction is quite exothermic in the absence of a solvent, but a temperature moderating effect is produced by the cooling effect of vigorous HZ evolution. Hence, by effective control $PZ_3$ addition, the reaction may be made self-regulating in the temperature range between 5–15 degrees centigrade.

Desirable solvents that may be utilized are neutral solvents. Typical solvents are toluene, heptane, xylene, methylene chloride, choroform, and benzene. Preferred solvents are methylene chloride, heptane, or xylene.

After the reaction has gone to completion, the bulk of the by-product HZ such as HCl, may optionally be removed by gently raising the temperature of the product to room temperature to about 50 degrees centigrade. The solvent utilized is removed, typically by application of a vacuum, to yield the remaining intermediate phosphorohalidite product.

To produce the phosphite ester stabilizer of the present invention, the above intermediate phosphorohalidite product is next reacted with a hydroxyaryl compound of the formula:

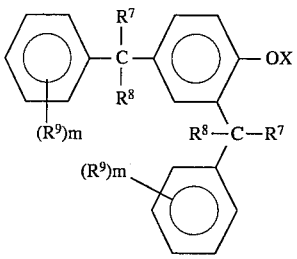

wherein $R^7$, $R^8$, $R^9$ and m are as described above. Suitable reaction methods are set out in Great Britain Patent 2087399A, Spivak et al. U.S. Pat. No. 4,318,845 issued 1982, and Article in Phosphorous & Sulfur Journal by J. D. Spivak et al. 1983, vol. 15, pp. 9–13, all of which are incorporated herein by reference.

The reaction between the intermediate phosphorohalidite product and the hydroxyaryl compound may be conducted in the same reaction vessel that was employed to produce the crude phosphite ester stabilizer by merely introducing the hydroxyaryl compound into the reactor. The reaction may be carried out at a suitable temperature between 20 to 150 degrees centigrade and preferably between about 35 to about 125 degrees Centigrade. The pressure of the reaction system is maintained between about 50 millimeters mercury absolute to atmospheric pressure. Typical reaction times to substantial completion are from 1 to about 24 hours. Preferably, the temperature and pressure conditions are selected to afford the maximum amount of product within time period of about 1 to about 10 hours.

The final proportions of reactants are at least approximately stoichiometric. It is desirable to work with at least a slight stoichiometric excess of one of the reactants.

The reaction is desirable conducted in the presence of a base such as an amine acceptor since $R_1$ is an alkyl group. The amine may be any amine which scavenges hydrogen chloride and/or hydrogen bromide as the case may be. The amine may be aliphatic, cyclic or aromatic. A single amine or a mixture of amines may be used as desired. The cyclic amines usually contain at least about 5 carbon atoms, preferably from 5 to about 10 carbon atoms. Examples include N-methylpyrrolidine, N-methylpiperidine, and N-phenylmorpholine, and 1,8-diazabicyclo[5,4,0]undec-7-one. The aromatic amines frequently contain at lest 5 carbon atoms with 5 to 15 being preferred. Examples include N,N-dimethylanilines, N,N-dimethylxylidines, pyridine, and alkyl derivative of pyridine. These may include polymer supported amines.

In most cases the amine employed contains at least 3 carbon atoms. Usually the amine contains from 3 to about 18 carbon atoms. The preferred amine acceptors are trialkyl amines with tripropyl amine, tributyl amine, and triheptyl amine being most preferred. When $R_1$ is a tert-alkyl group, such as t-butyl, then a stoichiometric amount of amine acceptor is desirable present.

After completion of the reaction, the amine acceptor present in the reaction mixture may be removed by the addition of a solvent. Typical solvents suitable for this purpose are hindered alcohols with isopropyl alcohol being preferred. The amine acceptor in the reaction mixture is solubilized by the solvent and removed from the reaction mixture to leave a remaining phosphite stabilizer which may be recovered in purified form by distillation, or crystallization. Typically the biphenyl bisphosphite ester may be crystallized or distilled from a suitable organic solvent such as toluene or heptane. It is also contemplated that the biphenyl phosphite may be solubilized by a suitable solvent, removed from the reaction mixture, and then separated from the solvent.

When the phosphite stabilizer is isolated in crystalline form, the present invention contemplates that it may be utilized in solid amorphous form. The amorphous phosphite composition is formed by rapid cooling of melt of the phosphite. Such melt may be a mixture of the phosphite and polyamine which is rapidly cooled to form a solid amorphous phosphite composition. The amorphous nature of composition enhances the hydrolytic stability of the solid composition compared to crystalline composition containing the same constituents, such compositions may additionally contain respective amounts of an amine preferably an aliphatic polyamine.

The amorphous composition is prepared by melting the crystalline phosphite, or a blend of the crystalline phosphite and an amine or other desired ingredients, to form a melt blend. The resulting melt blend is cooled to form an amorphous solid phosphite composition. The process may also involve storing the phosphite for a period in excess of 10 days (possibly in humid conditions (>60% relative humidity)) at ambient temperature, and then compounding the phosphite composition with a thermoplastic polymer such as a polyolefin, for example polypropylene for thermal oxidative stability thereof.

The amorphous stabilizer composition of the present invention preferably comprises at least 50 percent by weight of the phosphite based on the total weight of the stabilizer composition, more preferably comprises from 80 percent by weight to 99.9 percent by weight of the phosphite based on the total weight of the stabilizer composition, more preferably from 90 to 99.8 percent by weight thereof, more preferably from 95 to 99.5 percent by weight thereof, and most preferably from 97 to 99 percent by weight thereof.

A preferred additive is an amine. The amine is preferably present at a level of from 0.1 to 10 percent by weight based on the total weight of the stabilizer composition, more preferably from 0.2 to 10 percent by weight thereof, more preferably present at a level of from 0.6 to 5 percent by weight thereof, and most preferably from 1 to 3 percent by weight thereof. Such stabilizer amine compositions are preferably in the form of amorphous (non-crystalline) particles, such as powders and pellets.

The preferred amine additives are polyamines, and more preferably aliphatic polyamines. The aliphatic polyamine preferably has a boiling point of greater than 175° C., more preferably greater than 190° C., and most preferably greater than 200° C. The aliphatic polyamine may contain primary, secondary or tertiary amine groups. Preferably the amine groups are primary amine groups. The polyamine may contain 2, 3 or more amine groups, and in other words may be a diamine, triamine or greater polyamine amine. The preferred polyamines are aliphatic primary diamines of the formulas

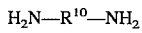

wherein $R^{10}$ is selected from $C_6$ to $C_{10}$ divalent alkyl groups, and more preferably the diamine is selected from 1,6 diaminohexane and 1,10-diaminodecane. Suitable aliphatic secondary diamines may be represented by the general formula:

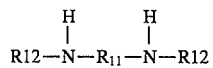

wherein $R^{11}$ is selected from $C_1$ to $C_{10}$ divalent alkyl groups and $R^{12}$ is selected from $C_1$ to $C_{30}$ monovalent alkyl group. Suitable aliphatic tertiary diamines may be represented by the general formula

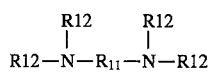

wherein $R^{11}$ and $R^{12}$ are defined as above. Most preferably the polyamine is an aliphatic primary diamine. The amines may also be monoamines and hydroxylamines such as triisopropanolamine, and $R^{12}NH_2$, $R^{12}_2NH$, $R^{12}_3N$, $R^{12}_2NOH$.

The stabilizer composition preferably contains less than 10 percent by weight of other materials, and more preferably less than 5 percent by weight, and most preferably less than 1 percent by weight additional ingredients.

Other ingredients may be polymeric materials and other organic materials such as waxes, synthetic and petroleum dried lubricating oils and greases; animal oils such as for example fat, tallow, lard, cod liver oil, sperm oil; vegetable oil such as caster, linseed, peanut, cod seed, and the like; fuel oil, diesel oil, gasoline, and the like. In other words, the stabilizer composition, is preferably substantially free of other materials, in other words, containing less than 1 percent of other organic materials, and more preferably is free of other organic materials. Optionally, the stabilizer composition is essentially free of monoamines, such as triisopropylamine. The compositions of the present invention are preferably amorphous to ensure homogeneity of the compositions. The present compositions are preferably obtained by melt mixing rather than simple mechanical blending or solution blending, and surprisingly and unexpectedly the compositions made by melt mixing show superior hydrolyric stability over similar compositions made by simple mechanical (dry) or solution blending.

The present invention also is a stabilized polymer composition which includes an effective amount of the phosphite described above. An amount of the phosphite of the invention is considered to be an "effective amount" when the polymer composition containing the phosphite of the invention shows improved stability in any of its physical or color properties in comparison to an analogous polymer composition which does not include a phosphite of the invention. In most polymer compositions, however, it will be preferred that the phosphites be present in an amount equal to about 0.01 to about 2 parts by weight per 100 parts by weight resin (phr). Amounts of about 0.01 to about 1 phr are more preferred, although most compositions will contain about 0.025 phr or more. The polymer composition may be thermoset in nature including unsaturated polyesters, phenolics, epoxy, urethanes, coating resins and crosslinkable latexes.

The polymer may also be any thermoplastic known in the art, such as polyesters, polyurethanes, polyalkylene terephthalates, polysulfones, polyimides, polyphenylene ethers, styrenic polymers, polycarbonates, acrylic polymers, polyamides, polyacetals, halide containing polymers and polyolefin homopolymers and copolymers. Mixtures of different polymers, such as polyphenylene ether/styrenic resin blends, polyvinyl chloride/ABS or other impact modified polymers, such as methacrylonitrile and alphamethylstyrene containing ABS, and polyester/ABS or polycarbonate/ABS and polyester plus some other impact modifier may also be used. Such polymers are available commercially or may be made by means well known in the art. However, the phosphites of the invention are particularly useful in thermoplastic polymers, such as polyolefins, polycarbonates, polyesters, polyphenylene ethers and styrenic polymers, due to the extreme temperatures at which thermoplastic polymers are often processed and/or used.

Polymers of monoolefins and diolefins, for example polypropylene, polyisobutylene, polybutene-1, polymethylpentene-1, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE) and linear low density polyethylene (LLDPE) may be used. Mixtures of these polymers, for example, mixtures of polypropylene with polyisobutylene, polypropylene with polyethylene (for example PP/HDPE, PP/LDPE) and mixtures of different types of polyethylene (for example LDPE/HDPE), may also be used. Also useful are copolymers of monoolefins and diolefines with each other or with other vinyl monomers, such as, for example, ethylene/propylene, LLDPE and its mixtures with LDPE, propylene/butene-1, ethylene/hexene, ethylene/ethylpentene, ethylene/heptene, ethylene/octene, propylene/isobutylene, ethylene/butane-1, propylene/butadiene, isobutylene, isoprene, ethylene/alkyl acrylates, ethylene/alkyl methacrylates, ethylene/vinyl acetate (EVA) or ethylene/acrylic acid copolymers (EAA) and their salts (ionomers) and terpolymers of ethylene with propylene and a diene, such as hexadiene, dicyclopentadiene or ethylidene-norbornene; as well as mixtures of such copolymers and their mixtures with polymers mentioned above, for example polypropylene/ethylene propylene-copolymers, LDPE/EVA, LDPE/EAA, LLDPE/EVA and LLDPE/EAA.

Thermoplastic polymers may also include styrenic polymers, such as polystyrene, poly-(p-methylstyrene), poly-(α-methylstyrene), copolymers of styrene or α-methylstyrene with dienes or acrylic derivatives, such as, for example, styrene/butadiene, styrene/acrylonitrile, styrene/alkyl methacrylate, styrene/maleic anhydride, styrene/butadiene/ethylacrylate/styrene/acrylonitrile/methylacrylate, mixtures of high impact strength from styrene copolymers and another polymer, such as, for example, from a polyacrylate, a diene polymer or an ethylene/propylene/diene terpolymer; and block copolymers of styrene, such as, for example, styrene/-butadiene/styrene, styrene/isoprene/styrene, styrene/ethylene/butylene/styrene or styrene/ethylene/propoylene styrene. Styrenic polymers may additionally or alternatively include graft copolymers of styrene or alphamethylstyrene such as, for example, styrene on polybutadiene, styrene on polybutadiene-styrene or polybutadiene-acrylonitrile; styrene and acrylonitrile (or methacrylonitrile) on polybutadiene and copolymers thereof; styrene and maleic anhydride or maleimide on polybutadiene; sytrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures of with the styrenic copolymers indicated above.

Nitrile polymers are also useful in the polymer composition of the invention. These include homopolymers and copolymers of acrylonitrile and its analogs, such as polymethacrylonitrile, polyacrylonitrile, acrylonitrile/-butadiene polymers, acrylonitrile/alkyl acrylate polymers, acrylonitrile/alkyl methacrylate/butadiene polymers, and various ABS compositions as referred to above in regard to styrenics.

Polymers based on acrylic acids, such as acrylic acid, methacrylic acid, methyl methacrylic acid and ethacrylic acid and esters thereof may also be used. Such polymers include polymethylmethacrylate, and ABS-type graft copolymers wherein all or part of the acrylonitrile-type monomer has been replaced by an acrylic acid ester or an acrylic acid amide. Polymers including other acrylic-type monomers, such as acrolein, methacrolein, acrylamide and methacrylamide may also be used.

Halogen-containing polymers may also be useful. These include resins such as polychloroprene, epichlorohydrin homo-and copolymers, polyvinyl chloride, polyvinyl bromide, polyvinyl fluoride, polyvinylidene chloride, chlorinated polyethylene, chlorinated polypropylene, florinated polyvinylidene, brominated polyethylene, chlorinated rubber, vinyl chloride-vinylacetate copolymers, vinyl chloride-ethylene copolymer, vinyl chloride-propylene copolymer, vinyl chloride-styrene copolymer, vinyl chloride-isobutylene copolymer, vinyl chloride-vinylidene chloride copolymer, vinyl chloride-styrene-maleic anhydride tercopolymer, vinyl chloride-styrene-acrylonitrile copolymer, vinyl chloride-butadiene copolymer, vinyl chloride isoprene copolymer, vinyl chloride-chlorinated propylene copolymer, vinyl chloride-vinylidene chloride-vinyl acetate tercopolymer, vinyl chloride-acrylic acid ester copolymers, vinyl chloride-maleic acid ester copolymers, vinyl chloride-methacrylic acid ester copolymers, vinyl chloride-acrylonitrile copolymer and internally platicized polyvinyl chloride.

Other useful thermoplastic polymers include homopolymers and copolymers of cyclic ethers, such as polyalkylene glycols, polyethylene oxide, polypropylene oxide or copolymers thereof with bis-glycidyl ethers; polyacetals, such as polyoxymethylene and those polyoxymethylene which contain ethylene oxide as a comonomer; polyacetals modified with thermoplastic polyurethanes, acrylates or methacrylonitrile containing ABS; polyphenylene oxides and sulfides, and mixtures of polyphenylene oxides with polystyrene or polyamides; polycarbonates and polyester-carbonates; polysulfones, polyethersulfones and polyetherketones; and polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-2(2,2,4(4-hydroxyphenyl)-propane) terephthalate and polyhydroxybenzoates as well as block-copolyetheresters derived from polyethers having hydroxyl end groups.

Polyamides and copolyamides which are derived from diamines and dicarboxylic acids and/or from aminocarboxylic acids or the corresponding lactams, such as polyamide, 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylene diamine and isophthalic or/and terephthalic acid and optionally an elastomer as modifier, for example poly-2,4,4-trimethylhexamethylene terephthalamide or poly-m-phenylene isophthalamide may be useful. Further copolymers of the aforementioned polyamides with polyolefins, olefin copolymers, ionomers or chemically bonded or grafted elastomers; or with polyethers, such as for instance, with polyethylene glycol, polypropylene glycol or polytetramethylene glycols and polyamides or copolyamides modified with EPDM or ABS may be used.

Polyolefin, polyalkylene terephthalate, polyphenylene ether and styrenic resins, and mixtures thereof are more preferred, with polyethylene, polypropylene, polyethylene terephthalate, polyphenylene ether homopolymers and copolymers, polystyrene, high impact polystyrene, polycarbonates and ABS-type graft copolymers and mixtures thereof being particularly preferred.

The resulting stabilized polymer compositions of the invention may optionally also contain various conventional additives, such as the following:

1. Antioxidants 1.1 Alkylated monophenols, for example: 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(alpha-methylcyclohexyl)-4,6 dimethylphenol, 2,6-di-octadecyl-4-methylphenol, 2,4,6,-tricyclohexyphenol, 2,6-di-tert-butyl-4-methoxymethylphenol.

1.2 Alkylated hydroquinones, for example, 2,6-di-tert-butyl-4-methoxyphenol, 2,5-di-tert-butyl-hydroquinone, 2,5-di-tert-amyl-hydroquinone, 2,6-diphenyl-4octadecyloxyphenol.

1.3 Hydroxylated thiodiphenyl ethers, for example, 2,2'-thio-bis-(6-tert-butyl-4-methylphenol), 2,2'-thio-bis-(4-octylphenol), 4,4'thio-bis-(6-tert-butyl-3-methylphenol), 4,4'-thio-bis-(6-tert-butyl-2-methylphenol).

1.4 Alkylidene-bisphenols, for example, 2,2'-methylene-bis-(6-tert-butyl-4-methylphenol), 2,2'-methylene-bis-(6-tert-butyl-4-ethylphenol), 2,2'-methylene-bis-(4-methyl-6-(alpha-methylcyclohexyl(phenol), 2,2'-methylene-bis-(4-methyl-6-cyclohexylphenol), 2,2'-methylene-bis-(6-nonyl-4-methylphenol), 2,2'-methylene-bis-(6-nonyl-4-methylphenol), 2,2'-methylene-bis-(6-(alpha-methylbenzyl)-4-nonylphenol), 2,2'-methylene-bis-(6-(alpha,alpha-dimethylbenzyl)-4-nonyl-phenol). 2,2'-methylene-bis-(4,6-di-tert-butylphenol), 2,2'-ethylidene-bis-(6-tert-butyl-4-isobutylphenol), 4,4'-methylene-bis-(2,6-di-tert-butylphenol), 4,4'-methylene-bis-(6-tert-butyl-2-methylphenol), 1,1-bis-(5-tert-butyl-4-hydroxy-2-methylphenol)butane. 2,6-di-(3-tert-butyl-5-methyl-2-hydroxybenzyl)-4-methylphenol, 1,1,3-tris-(5-tert-butyl-4-hydroxy-2-methylphenyl)butane, 1,1-bis-(5-tert-butyl-4-hydroxy-2-methylphenyl)-3-dodecyl-mercaptobutane, ethyleneglycol-bis-(3,3,-bis-(3'-tert-butyl-4'-hydroxyphenyl)-butyrate)-di-(3-tert-butyl-4-hydroxy-5-methylphenyl)-dicyclopentadiene, di-(2-(3'-tert-butyl-2'hydroxy-5'methylbenzyl)-6-tert-butyl-4-methylphenyl)terephthalate, and other phenolics such as mono-acrylate esters of bisphenols such as ethylidiene bis-2,4-di-t-butyl phenol monoacrylate ester.

1.5 Benzyl compounds, for example, 1,3,5-tris-(3,5-di-tert-butyl-4-hydroxybenzyl)-2,4,6-trimethylbenzene, bis-(3,5-di-tert-butyl-4-hydroxybenzyl)sulfide, isooctyl 3,5-di-tert-butyl-4-hydroxybenzyl-mercaptoacetate, bis-(4-tert-butyl-3-hydroxy-2,6-dimethylbenzyl)dithiol-terephthalate. 1,3,5-tris-(3,5-di-tert-butyl-4-hydroxybenzyl)isocyanurate. 1,3,5-tris-(4-tert-butyl-3-hydroxy-2,6-dimethylbenzyl)isocyanurate, dioctadecyl 3,5-di-tert-butyl-4-hydroxybenzyl-phosphonate, calcium salt of monoethyl 3,5-di-tert-butyl-4-hydroxybenzylphosphonate, 1,3,5-tris-(3,5-dicyclohexyl-4-hydroxybenzyl) isocyanurate.

1.6 Acylaminophenols, for example, 4-hydroxy-lauric acid anilide, 4-hydroxy-stearic acid amilide, 2,4-bis-octylmercapto-6-(3,5-tert-butyl-4-hydroxyanilino)-s-triazine, octyl-N-(3,5-di-tert-butyl-4-hydroxyphenyl)carbamate.

1.7 Esters of beta-(3,5-di-tert-butyl-4-hydroxyphenol)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thiodiethyleneglycol, di-hydroxyethyl oxalic acid diamide.

1.8 Esters of beta-(5-tert-butyl-4-hydroxy-3-methylphenyl)-propionic acid with monohydric or polyhydric alcohols, for example, methanol, diethyleneglycol, octadecanol, triethyleneglycol, 1,6-hexanediol, pentaerythritol, neopentylglycol, tris-hydroxyethyl isocyanurate, thidiethyleneglycol, dihydroxyethyl oxalic acid diamide.

1.9 Esters of beta-(5-tert-butyl-4-hydroxy-3-methylphenyl) propionic acid with mono-or polyhydric alcohols, e.g., with methanol, diethylene glycol, octadecanol, triethylene glycol, 1,6-hexanediol, pentaerythritol, neopentyl glycol, tris(hydroxyethyl) isocyanurate, thiodiethylene glycol, N,N-bis(hydroxyethyl) oxalic acid diamide.

1.10 Amides of beta-(3,5-di-tert-butyl-4-hydroxyphenol)-propionic acid for example, N,N'-di-(3,5-di-tert-butyl-4-hydroxyphenylpropionyl)hexamethylen-diamine, N,N'-di-(3,5-di-tert-butyl-4-hydroxyphenylpropionyl)trimethylenediamine, N,N'-di-(3,5-di-tert-butyl-4-hydroxyphenylpropionyl)-hydrazine.

2. UV absorbers and light stabilizers.

2.1 2-(2'-hydroxyphenyl)-benzotriazoles, for example, the 5'methyl-,3'5'-di-tert-butyl-,5'-tert-butyl-,5'(1,1,3,3-tetramethylbutyl)-,5-chloro-3',5'-di-tert-butyl-,5-chloro-3'tert-butyl-5'methyl-,3'sec-butyl-5'tert-butyl-,4'-octoxy,3',5'-ditertamyl-3',5'-bis-(alpha, alpha-dimethylbenzyl)-derivatives.

2.2 2-Hydroxy-benzophenones, for example, the 4-hydroxy-4-methoxy-,4-octoxy,4-decloxy-,4-dodecyloxy-,4-benzyloxy,4,2',4'-trihydroxy- and 2'hydroxy-4,4'-dimethoxy derivative.

2.3 Esters of substituted and unsubstituted benzoic acids for example, phenyl salicylate, 4-tert-butylphenyl-salicilate, octylphenyl salicylate, dibenzoylresorcinol, bis-(4-tert-butylbenzoyl)-resorcinol, benzoylresorcinol, 2,4-di-tert-butylphenyl-3,5-di-tert-butyl-4-hydroxybenzoate and hexadecyl-3,5-di-tert-butyl-4-hydroxybenzoate.

2.4 Acrylates, for example, alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or butyl ester, alpha-carbomethoxy-p-methoxy-cinnamic acid methyl ester, N-(beta-carbomethoxy-beta-cyano-vinyl)-2-methylindoline.

2.5 Nickel compounds, for example, nickel complexes of 2,2'-thio-bis(4-(1,1,1,3-tetramethylbutyl)-phenol), such as the 1:1 or 1:2 complex, optionally with additional ligands such as n-butylamine, triethanolamine or N-cyclohexyldiethanolamine, nickel dibutyldithiocarbamate, nickel salts of 4-hydroxy-3,5-di-tert-butylbenzylphosphonic acid monoalkyl esters, such as of the methyl, ethyl, or butyl ester, nickel complexes of ketoximes such as of 2-hydroxy-4-methyl-penyl undecyl ketoxime, nickel complexes of 1-phenyl-4-lauroyl-5-hydroxy-pyrazole, optionally with additional ligands.

2.6 Sterically hindered amines, for example bis-(2,2,6,6-tetramethylpiperidyl)-sebacate, bis-(1,2,2,6,6-pentamethylpiperidyl)-sebacate, n-butyl-3,5-di-tert-butyl-4-hydroxybenzyl malonic acid bis(1,2,2,6,6,-pentamethylpiperidyl)ester, condensation product of 1-hydroxyethyl-2,2,6,6-tetramethyl-4-hydroxy-piperidine and succinic acid, condensation product of N,N'-(2,2,6,6- tetramethylpiperidyl)-hexamethylendiamine and 4-tert-octylamino-2,6-dichloro-1,3,5-s-triazine, tris-(2,2,6,6-tetramethylpiperidyl)nitrilotriacetate, tetrakis-(2,2,6,6-tetramethyl-4-piperidyl)-1,2,3,4-butane-tetracarbonic acid, 1,1'(1,2-ethanediyl)-bis-(3,3,5,5-tetramethylpiperazinone). These amines typically called HALS (Hindered Amines Light Stabilizing) include butane teracarboxylic acid 2,2,6-tetramentyl piperidonol esters. Such amines include hydroxylamines derived from hindered amines, such as di(1-hydroxy-2,2,6,6-tetramethylpiperidin-4-yl)sebacate: 1-hydroxy 2,2,6,6-tetramethyl-4-benzoxypiperidine; 1-hydroxy-2,2,6,6-tetramethyl-4-(3,5-di-tert-butyl-4-hydroxy hydrocinnamoyloxy)-piperdine; and N-(1-hydroxy-2,2,6,6-tetramethyl-piperidin-4-yl)-epsiloncaprolactam.

2.7 Oxalic acid diamides, for examples, 4,4'-dioctyloxy-oxanilide, 2,2'-di-octyloxy-5',5'-di-tert-butyloxanilide, 2,2'-di-dodecyloxy-5',5'di-tert-butyloxanilide, 2-ethoxy-2'-ethyl-oxanilide, N,N'-bis(3-dimethylaminopropyl)oxalamide, 2-ethoxy-5-tert-butyl-2'-ethyloxanilide and its mixture with 2-ethoxy-2'ethyl-5,4-di-tert-butyloxanilide and mixtures of ortho-and para-methoxy-as well as of o-and p-ethoxy-disubstituted oxanilides.

3. Metal deactivators, for example, N,N'-diphenyloxalic acid diamide, N-salicylal-N'-salicyloylhydrazine, N,N'-bis-salicyloylhydrazine, N,N'-bis(3,5-di-tert-butyl-4-hydrophenylpropionyl)-hydrazine, salicyloylamino-1,2,4-triazole, bis-benzyliden-oxalic acid dihydrazide.

4. Phosphites and phosphonites, for example, triphenyl phosphite, diphenylalkyl phosphites, phenyldialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl)pentaerythritol diphosphite tristearyl sorbitol triphosphite, and tetrakis(2,4-di-tert-butylphenyl)4,4'-biphenylene diphosphonite.

5. Peroxide scavengers, for example, esters of betathiodipropionic acid, for example the lauryl, stearyl, myristyl or tridecyl esters, mercaptobenzimidazole or the zinc salt of 2-mercaptobenzimidazole, zinc-dibutyldithiocaramate, dioctadecyldisulfide, pentaerythritoltetrakis-(beta-dodecylmercapto)-propionate.

6. Polyamide stabilizers, for example copper salts in combination with iodides and/or phosphorus compounds and salts of divalent manganese.

7. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, Ca stearate, calcium stearoyl lactate, calcium lactate, Zn stearate, Mg stearate, Na ricinoleate and K palmitate, antimony pyrocatecholate or zinc pyrocatecholate, including neutralizers such as hydrotalcites and synthetic hydrotalcites, and Li, Na, Mg, Ca, Al hydroxy carbonates.

8. Nucleating agents, for example, 4-tert butylbenzoic acid, adipic acid, diphenylacetic acid, sodium salt of methylene bis-2,4-dibutylphenyl, cyclic phosphate esters, sorbitol tris-benzaldehyde acetal, and sodium salt of bis(2,4-di-t-butyl phenyl)phosphate.

9. Fillers and reinforcing agents, for example, calcium carbonate, silicates, glass fibers, asbestos, talc, kaolin, mica, barium sulfate, metal oxides and hydroxides, carbon black and graphite.

10. The present invention may also be used in conjunction with aminoxy propanoate derivatives such as methyl-3-(N,N-dibenzylaminoxy)propanoate; ethyl-3-(N,N-dibenzylaminoxy)propanonoate; 1,6-hexamethylene-bis(3-N,N-dibenzylaminoxy)proponoate); methyl-(2-(methyl)-3(N,N-dibenzylaminoxy)propanoate); octadecyl-3-(N,N-dibenzylaminoxy)propanoic acid; tetrakis (N,N-dibenzylaminoxy)ethyl carbonyl oxymethy)methane; octadecyl-3-(N,N-diethylaminoxy)-propanoate; 3-(N,N-dibenzylaminoxy)propanoic acid potassium salt; and 1,6-hexamethylene bis(3-(N-allyl-N-dodecyl aminoxy)propanoate).

11. Other additives, for example, plasticizers, epoxidized vegetable oils, such as epoxidized soybean oils, lubricants, emulsifiers, pigments, hydroxylamines such as $R_2NOH$ wherein R is a $C_1$ to $C_{30}$ alkyl group, such as propyl or stearyl, optical brighteners, flameproofing agents, anti-static agents, blowing agents and thiosynergists such as dilaurythiodipropionate or distearylthiodipropionate.

12. Nitrones, for example n-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-penta-decyl nitrone, n-octadecyl-alpha-heptadecylnitrone, N-hexadecyl-alpha-heptadecyl nitrone, N-octadecyl-alpha-pentadecy nitrone, N-heptadecyl-alpha-heptadecy nitrone, N-octadecyl-alpha-hexadecyl nitrone, nitrone derived from N,N-dialkylhydroxylamine derived from hydrogenated tallow amine.

Polymeric particles may be coated with the present stabilizer compositions alone or in combination with other stabilizers for stabilization of the polymeric material. Particles may be spherical in shape and may be made by processes such as "Reactor Granule Technology" as disclosed in P. Galli and J. C. Halock, The Reactor Granule—A Unique Technology for the Production of a New Generation of Polymer Blends, Society of Plastics Engineers, Polyolefin III International Conference Feb. 24–27, 1991 and as disclosed in Pedrazzeth et al. U.S. Pat. No. 4,708,979 entitled Process for the Stabilization of Spherically Polymerized Polyolefins issued Nov. 24, 1987 both of which are disclosed herein by reference. Particle formation may be achieved by support Ziegler-Natta Catalyst systems. Suitable commercial processes are known by the trademarks: Spheripol, Addipol and Spherilene.

Olefin polymers may be produced by polymerization of olefins in the presence of Ziegler-Natta catalysts optionally on supports such as but not limited to Mg $Cl_2$, chromium salts and complexes thereof, optionally supported on Silica or other materials. They may also be produced utilizing catalysts based on cyclopentadiene complexes of metals typically complexes of Ti and Zr.

Consistent with the invention, the amorphous stabilizer compositions of the invention may be added to the polymer at any time prior to or during fabrication into articles and may be combined with the polymer by any of a variety of means known in the art, such as by preblending or by being fed directly into fabrication equipment.

The following examples illustrate the present invention.

EXAMPLE 1

The phosphite ester having the following formula I:

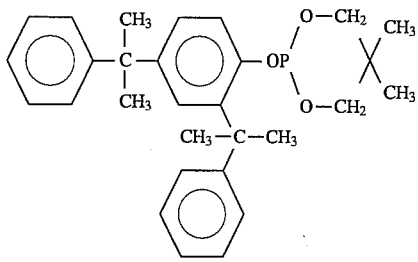

was prepared in the following manner. A 500 ml. 3-necked flask was fitted with a reflux water condenser and an addition funnel. 67.7 gram of neopentyl glycol and 300 ml. of methylene chloride was added to the flask. The flask was cooled to 0–5 degrees Centigrade by placing it into an ice/salt bath. 111.58 grams of phosphorous trichloride was placed in the addition funnel and was added slowly dropwise into the reaction flask during a 5 hour period while the temperature was maintained below 10 degrees centigrade. The flask was allowed to warm up to room temperature during a 2 hour period. Methylene chloride was distilled off and the pale yellow color liquid was vacuum distilled at 80 degrees Centigrade for 18 min. of Hg to collect 104.17 grams of pure colorless neopentyl glycol chlorophosphite for a yield of 95.08 percent. A 500 ml. 3-necked flask fitted with a temperature probe, a condenser, and an addition funnel. 66.09 gram of 2,4-dicumylphenol having the following formula:

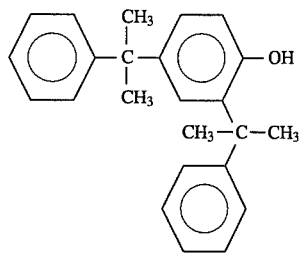

and 175 grams of tributylamine was added to the flask. The reaction mixture was stirred well with a mechanical stir shaft equipped with a teflon paddle. 34.15 grams of neopentylglycol monochlorophosphite dissolved in approximately 5.0 grams of toluene was placed in the addition funnel and was added into the reaction mixture during a 10 minute interval. An exothermic reaction occurred and the temperature reached approximately 46 degrees Centigrade. The reaction flask was heated slowly to 98 degrees Centigrade and held for about 4 hours. The reaction mixture was allowed to cool to room temperature. To separate the reaction product from the amine, 150 ml. of isopropyl alcohol was added into the reaction mixture and stirred. The reaction product was filtered through a sintered glass funnel. The liquid portion containing solubilized amine was separated and a remaining white colored product isolated. The crude mixture was stirred again in 150 ml. of isopropyl alcohol, filtered and dried to isolate 74.03 gram of the product at 80.02 percent yield. The product had the formula identified above. The melting point was 126–127 degrees Centigrade. A sample crystallized from heptane as white crystalline platelets had a melting point of 127–128 degrees Centigrade.

EXAMPLE 2

Following the above procedure of Example 1, a composition of the following formula II was prepared:

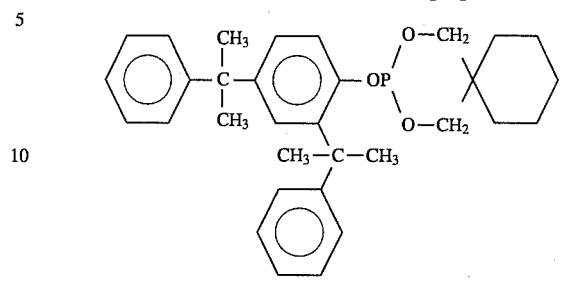

From 144.21 grams of cyclohexane-1,1-dimethanol, 137.33 grams of phosphorus trichloride as reactants in 250 grams of methylene chloride, 146.29 grams of cyclohexane-1,1-dimethanol chlorophosphite for a 93.04% yield was obtained as a colorless liquid upon vacuum distillation at 114°–116° Centigrade at 3.5 min. Following essentially the same procedure as set forth in Example 1, from 66.09 grams of 2-4-dicumylphenol, 114.0 grams of tributylamine, and 41.75 grams of cyclohexane-1,1-dimethyl alcohol chlorophosphite, 87.09 grams of phosphite product as set forth in the above formula at an 86.63% yield was obtained. The product had a melting point of 116°–118° Centigrade. A sample crystallized from heptane had a m.p. of 119°–120° Centigrade.

I claim:

1. A phosphite of the formula:

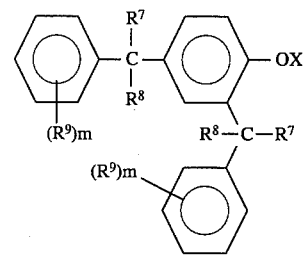

$R^7$ and $R^8$ are alkyl of from 1 to 6 carbon atoms, most preferably an unsubstituted alkyl group, $R^9$ is alkyl of 1 to 12 carbon atoms, m is from 0 to 5; and wherein X has the formula:

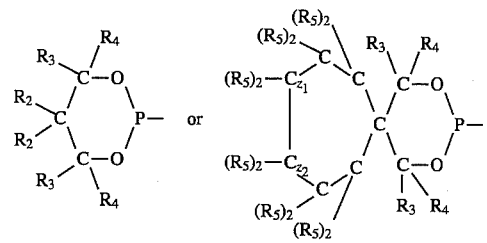

wherein $R_2$ is independently selected from the group consisting of alkyl groups having from 1 to 12 carbon atoms, and $R_3$, $R_4$ and $R_5$ are independently selected from the group consisiting of hydrogen, halogen, or alkyl of from 1 to 3 carbon atoms, and z is 0 or 1.

2. The phosphite of claim 1 wherein $R^7$ and $R^8$ are alkyl of from 1 to 3 carbon atoms, $R^9$ is alkyl of 1 to 4 carbon atoms, m is from 0 to 3.

3. The phosphite of claim 2 wherein X has the formula:

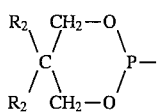

wherein $R_2$ is independently selected from straight chain alkyl groups having from 1 to 6 carbon atoms, or, the cyclic alkane moieties of the formulae:

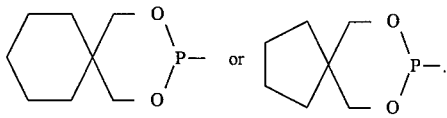

4. The phosphite composition of claim 3 wherein m is 0.

5. The phosphite composition of claim 3 having the formula:

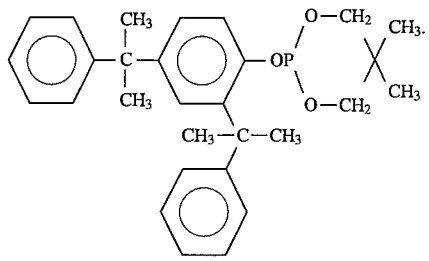

6. A themoplastic composition comprising a thermoplastic polymer and a stabilizing amount of a phosphite of the formula:

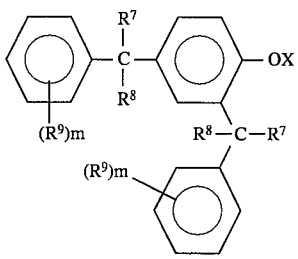

$R^7$ and $R^8$ are alkyl of from 1 to 6 carbon atoms, $R^9$ is alkyl of 1 to 12 carbon atoms, m is from 0 to 5; and wherein X has the formula:

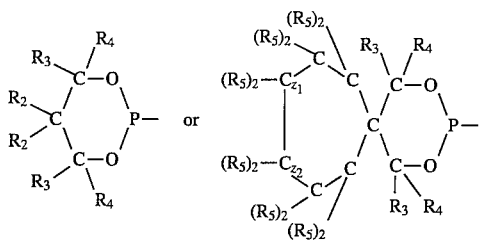

wherein $R_2$ is independently selected from the group consisting of alkyl groups having from 1 to 12 carbon atoms, and $R_3$, $R_4$ and $R_5$ are independently selected from the group consisiting of hydrogen, halogen, or alkyl of from 1 to 3 carbon atoms, and z is 0 or 1.

7. The thermoplastic composition of claim 6 wherein $R^7$ and $R^8$ are alkyl of from 1 to 3 carbon atoms, $R^9$ is alkyl of 1 to 4 carbon atoms, m is from 0 to 3.

8. The thermoplastic composition of claim 6 wherein X has the formula:

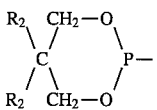

wherein $R_2$ is independently selected from straight chain alkyl groups having from 1 to 6 carbon atoms, or, the cyclic alkane moieties of the formulae:

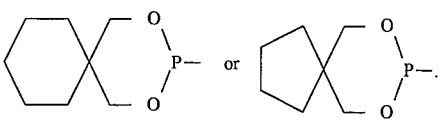

9. The thermoplastic composition of claim 6 wherein m is 0.

10. The thermoplastic composition of claim 6 having the formula:

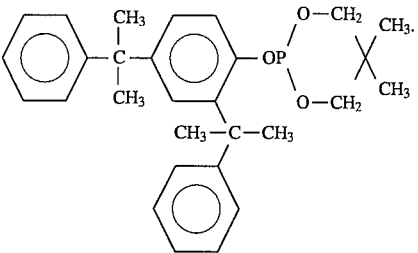

11. A thermoplastic composition as claimed in claim 6 comprising a thermoplastic resin and from 0.01 to 1.0 percent by weight of a phosphite composition based on the total weight of the composition.

12. A thermoplastic composition as claimed in claim 6 wherein said thermoplastic resin is selected from the group consisting of polyolefins, polycarbonates, polyesters, polyvinyl chloride and polystyrenes.

13. A thermoplastic composition as claimed in claim 6 wherein said thermoplastic resin is polypropylene.

14. A thermoplastic composition as claimed in claim 6 wherein said composition consists essentially of said thermoplastic resin and said phosphite.

* * * * *